United States Patent [19]

Fischel

[11] 4,017,190
[45] Apr. 12, 1977

[54] BLOOD LEAK DETECTOR COMPARING INTENSITIES OF HIGH ABSORPTION BAND AND LOW ABSORPTION BAND OF A SINGLE BEAM OF LIGHT PASSING THROUGH A SAMPLE

[76] Inventor: Halbert Fischel, 5301 Newcastle, No. 16, Encino, Calif. 91316

[22] Filed: July 18, 1975

[21] Appl. No.: 597,243

[52] U.S. Cl. .............................. 356/178; 210/96 R; 210/321 R; 340/242; 356/181; 356/184
[51] Int. Cl.² .................................... G01J 3/46
[58] Field of Search ....... 210/321 R, 96; 340/242; 356/39, 40, 41, 51, 184, 189, 206; 246/178

[56] References Cited

UNITED STATES PATENTS

| | | | |
|---|---|---|---|
| 3,405,268 | 10/1968 | Brunton | 356/51 |
| 3,441,136 | 4/1969 | Serfass et al. | 210/321 |
| 3,514,210 | 5/1970 | Hrdina | 356/246 |
| 3,632,211 | 1/1972 | Sedivy et al. | 356/41 |
| 3,734,631 | 5/1973 | Justice et al. | 356/51 |
| 3,799,672 | 3/1974 | Vurek | 356/41 |
| 3,832,067 | 8/1974 | Kopf et al. | 356/181 |
| 3,847,483 | 11/1974 | Shaw et al. | 356/41 |
| 3,887,281 | 6/1975 | Kurita et al. | 356/189 |

Primary Examiner—Vincent P. McGraw
Attorney, Agent, or Firm—Fraser and Bogucki

[57] ABSTRACT

A system for detecting small amounts of hemoglobin in a solution detects the ratio between the light transmissivities at separated wavelengths of a sample solution, one of which wavelengths is in a range at which hemoglobin is highly light absorptive. Through the use of the ratios of the signals, a reading of high sensitivity and linearity is provided in the presence of substantial contamination and turbidity in the sample or the system.

17 Claims, 4 Drawing Figures

WAVE-LENGTH, MICRONS

ABSORPTION SPECTRA. 1. HEMOGLOBIN
2. OXYHEMOGLOBIN

BLOOD LEAK DETECTOR COMPARING INTENSITIES OF HIGH ABSORPTION BAND AND LOW ABSORPTION BAND OF A SINGLE BEAM OF LIGHT PASSING THROUGH A SAMPLE

BACKGROUND OF THE INVENTION

1. Field of the Invention

This invention relates to a blood leak detector and more particularly to a detector which passes light through a sample solution and indicates the ratio of light passing through the sample at frequencies of high blood absorption to light passing through the sample at frequencies of low blood absorption.

2. Description of the Prior Art

In a number of known clinical systems, such as hemodialysis systems, it is desirable and sometimes necessary to detect the presence of small amounts of blood in a clinical solution. In the hemodialysis system, for example, the presence of blood in the salt solution utilized for dialysis indicates leakage through the dialyzer membrane or some other point in the system. Leakage in a very small proportionality (e.g. concentrations from 0.25 to 7.0 mg % of hemoglobin (hb)) must be detected in order to sound an alarm to indicate a system malfunction.

Known blood leak detection systems typically operate in response to the difference between a sample reading that is responsive to turbidity of the solution, and a reference reading which represents the average broadband light output of the lamp source. Using the broadband or some other average characteristic of the light source as a reference, the different reading provided by the turbidity-responsive sampling provides a signal indicating the presence of hemoglobin in the blood. However, contamination of the windows in the optical path or any source of turbidity which usually collects during the course of dialysis tends to diminish the reading channel intensity, substantially affecting the accuracy of the measurement that is provided. Similarly, the presence of other turbidity than hemoglobin can effect the reference level, as can the light output of the illuminating source, which tends to diminish with aging of the lamp. It is possible to compensate, at extra expense, for lamp aging effects and for other reference signal variations by servo techniques which, for example, increase lamp energization current in order to tend to maintain a constant illumination output. However, it is still not feasible to provide a highly sensitive output that is relatively unaffected by contamination and turbidity effects.

Other problems in known systems relate to automatic response to alarm conditions. On a typical blood dialysis system the dialyzer must be bypassed and the detector flushed upon the detection of blood. However, flushing of the detector eliminates the alarm condition to cause the system to oscillate between normal and alarm operation modes. In at least one system that is protected against oscillation, it is extremely difficult to restart normal operation once an alarm condition is detected.

SUMMARY OF THE INVENTION

Blood responsive detectors in accordance with the present invention optically sample, from a common light source, the light transmitted at two wavelength regions, one of which is highly responsive to the absorption effect of hemoglobin. The ratio of the signals derived at these two wavelength regions is determined, and this ratio represents with accuracy and freedom from noise effects the presence of small amounts of hemoglobin in the sample solution.

In a more particular example of a system in accordance with the invention, the light transmissivity of a sample solution at approximately 4200 A and a broader band encompassing 5000 A is derived by suitable optical filtering at separate photoresistive elements. To determine the ratio between these readings, one photoresistive photosensor element is coupled in the input circuit of an operational amplifier, with the other photoresistive photosensor element being coupled in the feedback circuit of the operational amplifier, with the amplifier output then representing a high gain counterpart of the hemoglobin concentration. In accordance with more specific aspects of the invention, the output signal current is linearized and then converted to a voltage which may both drive an indicator and be compared to a selectable voltage level in alarm circuits which provide a lamp and signal indication when selectable limits are exceeded.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
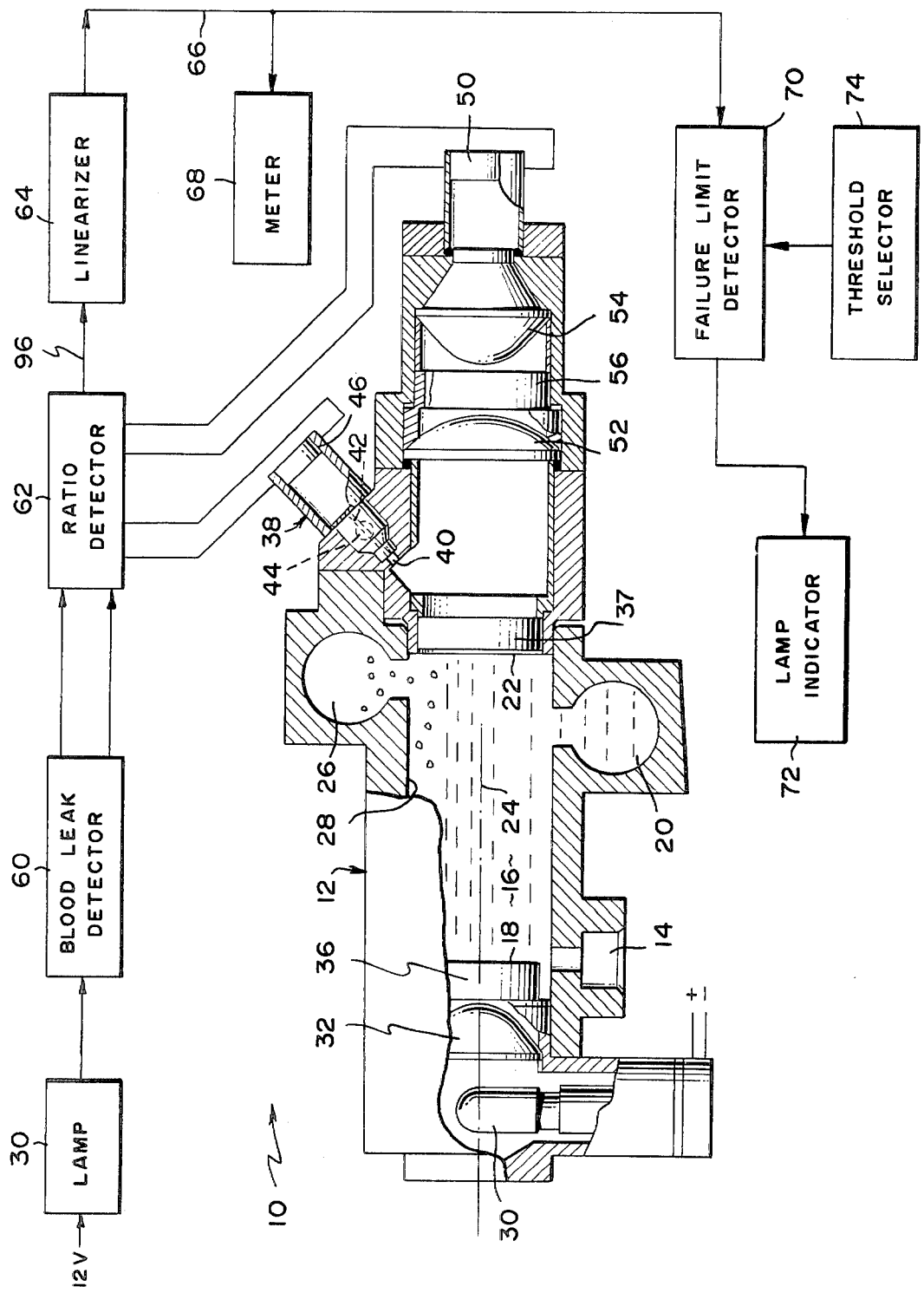
FIG. 1 is a combined sectional and block diagram representation of a blood leak detector system in accordance with the invention.
Figure 2:
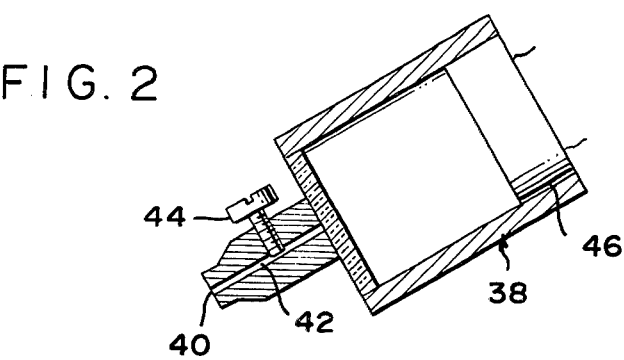
FIG. 2 is an enlarged fragmentary view of a light sensing channel in accordance with the invention.

Referring now to FIG. 1 an exemplification of a blood leak detector system 10 in accordance with the invention disposes a photosensing system within a generally cylindrical housing 12, in association with electronics which provide desired measurement, display and alarm functions. In the system, an effluent sample is passed through an input port 14 into an observation channel that is cylindrical in form and not quite horizontally disposed, the solution inlet 14 being on the underside of the observation channel 16 proximate a lower end 18 thereof and a solution outlet 20 being spaced apart along the length of the channel 16 and on the upper end 22 relative to a horizontal axis 24. This slightly upward tilted disposition permits the relatively slow moving fluid to be retained within the channel 16 while bubbles in the effluent sample move rapidly from the inlet 14 to a bubble outlet 26 proximate an upper chamber surface 28 and the upper end 22 and therefore have minimum effect on the readings taken.

A lamp 30 is energized from a suitable power source and is disposed at one end of the housing 12 along the axis 24 of the observation channel 16, and light is directed through a concentrator lens 32 along the length of the observation channel 16 through transmissive windows 36, 37 which form the ends 18, 22 in conventional fashion. Adjacent the exterior side of the downstream window 36 at end 18 relative to the observation channel is disposed a ground glass which scatters the incident light on the air side of the observation channel 16.

An angularly disposed first photodetection system 38 on the side of the housing 12 opposite the light source 30 detects the average light intensity of the emissions from the diffuse light source represented by the light scattering window 36 which pass through chamber 16. System 38 forms an optical channel 40 having a relatively long, small cross-sectional pinhole light path 42. An adjustable screw 44 intercepts the pinhole light path 42 to an extent determined by the position of screw 44. Thus, screw 44 permits control of aperture size and adjustment of the normal light intensity incident on a reference photocell 46 which responds to the average light level at the ground glass, including light at frequencies not readily absorbed by blood. The adjustment of screw 44 is preferably made with clear fluid within chamber 16.

Figure 3:
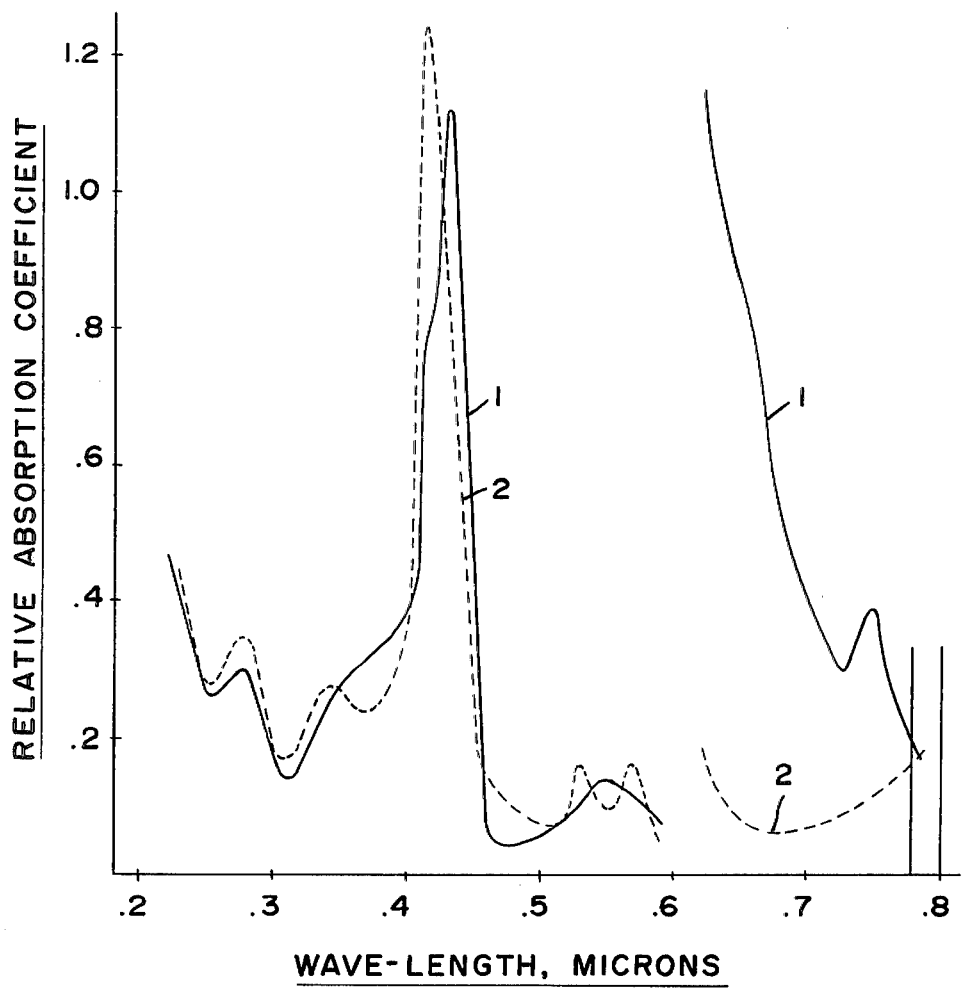
FIG. 3 is a graphical representation of light absorption characteristics of hemoglobin and oxyhemoglobin.

Along the main axis 24 of the observation channel, at the opposite end of the housing 12 from the lamp 30 there is disposed a sample photocell 50, which may be referred to as the blue photocell. Cell 50 receives light from the ground glass 36 that is passed through chamber 16 past optical channel 40 and through a pair of focusing lenses 52, 54 which are separated by a blue filter 56 which has a narrow bandpass characteristic at light frequencies having a wavelength of approximately 4200 A. This bandpass characteristic corresponds to the light absorption characteristic of the hemoglobin constituent of blood as depicted in FIG. 3, which is representative of a graph shown in an article, "Hemoglobin-Oxygen Equilibrium," *Journal of Biological Chemistry*, Vol. 123, p. 335 at 342 (1938), A. E. Sidwell Jr., R. H. Munch, E. S. G. Barron, and T. R. Hogness.

The light detected by the reference photocell may be referred to as white light, inasmuch as it is responsive to color constituents both below and above the 4200 A wavelength at which hemoglobin and oxyhemoglobin provide greatest light attenuation. In actuality, however, as shown by the published data shown in FIG. 3, the least attenuation of the spectro band occurs in the region of 4700 A to 5000 A, so that the reference photocell should be responsive to frequencies of light passing through chamber 16 in this band. This low attenuation factor provides a significant benefit because the relatively close spacing between the reference and the blue photocell channels, in terms of wavelength response, means that as the lamp characteristics change both channels are affected substantially equally. Also, non-spectral changes in characteristics, i.e. the gray level, affect both channels substantially equally.

Referring to the block diagram portion of FIG. 1, lamp 30 illuminates blood leak detector 60 which includes the two photocells 46, 50. Both of the photocells are photosensors of the photoresistive type, and each is coupled in a ratio detector circuit 62 which provides a varying voltage level signal representing the ratio of the blue light with respect to the white light samples to a linearizer circuit 64 which improves the accuracy of the reading across the entire range. The output signal 66 from the linearizer is coupled to drive an adjustable meter 68 and may provide a direct reading of blood concentration in standard terms such as milligram percent, or milligrams of hemoglobin per 100 cc of solution. The output signal 66 is also coupled to alarm circuits which include a failure limit detector 70 which actuates an indicator lamp 72 to provide an output alarm signal in the event that either a preset level determined by threshold selector 74 or a fixed maximum level is exceeded.

In the operation of the system of FIG. 1, the effluent sample passing from the inlet 14 to the outlet 20 through the observation channel 16 is illuminated by the light from the lamp 30 which falls on the ground glass screen on the air side of the observation channel as concentrated by the lens system and attenuated by the turbidity factors in the observation channel 16, including the hemoglobin and oxyhemoglobin constituents of the blood that may be present. The variable size aperture is adjusted to a selected zero setting at which the resistances of cells 46 and 50 are equal while a clear liquid is within chamber 16. The values of the variable resistances represented by the reference photocell 46 and the blue photocell 50 are determined by the broadband illumination of the reference photocell 46 and the blue filtered illumination of the blue photocell 50. In the ratio detector 62, an output voltage $V_o$ is determined by the ratios of the states of the two photocells in accordance with the equation:

$$V_o = -R_b/R_{ref} \times V_I,$$

where $V_I$ is the input voltage to the reference photocell, $R_b$ is the resistance of the blue photocell, and $R_{ref}$ is the resistance of the reference photocell.

Significant benefits are derived by the use of the ratio relationship and the 4200 A bandpass filter in the manner described. The presence of a minute amount of blood sharply diminishes the signal at the blue photocell, while having only a minor effect at the reference photocell. A concentration of 7 mg. % Hb affects the blue channel approximately 100 times greater than the reference channel. The net result is a 100:1 ratio between the input and output voltages, as opposed to a mere difference between the readings, which could be several orders of magnitude less depending upon initial input voltages and light levels. Changes in the spectral characteristics or in the gray level of the system affect both channels equally and have little effect on the ratio. Thus the system is actually sensing blood property, and is substantially unaffected by contamination and turbidity, whether caused by dirt on the windows or turbidity of other kinds than blood matter in the sample effluent.

The output signal from the ratio detector is amplified over the input signal with considerable gain, and is linearized in the linearizer circuits, which provide a varying current level output.

Figure 4:
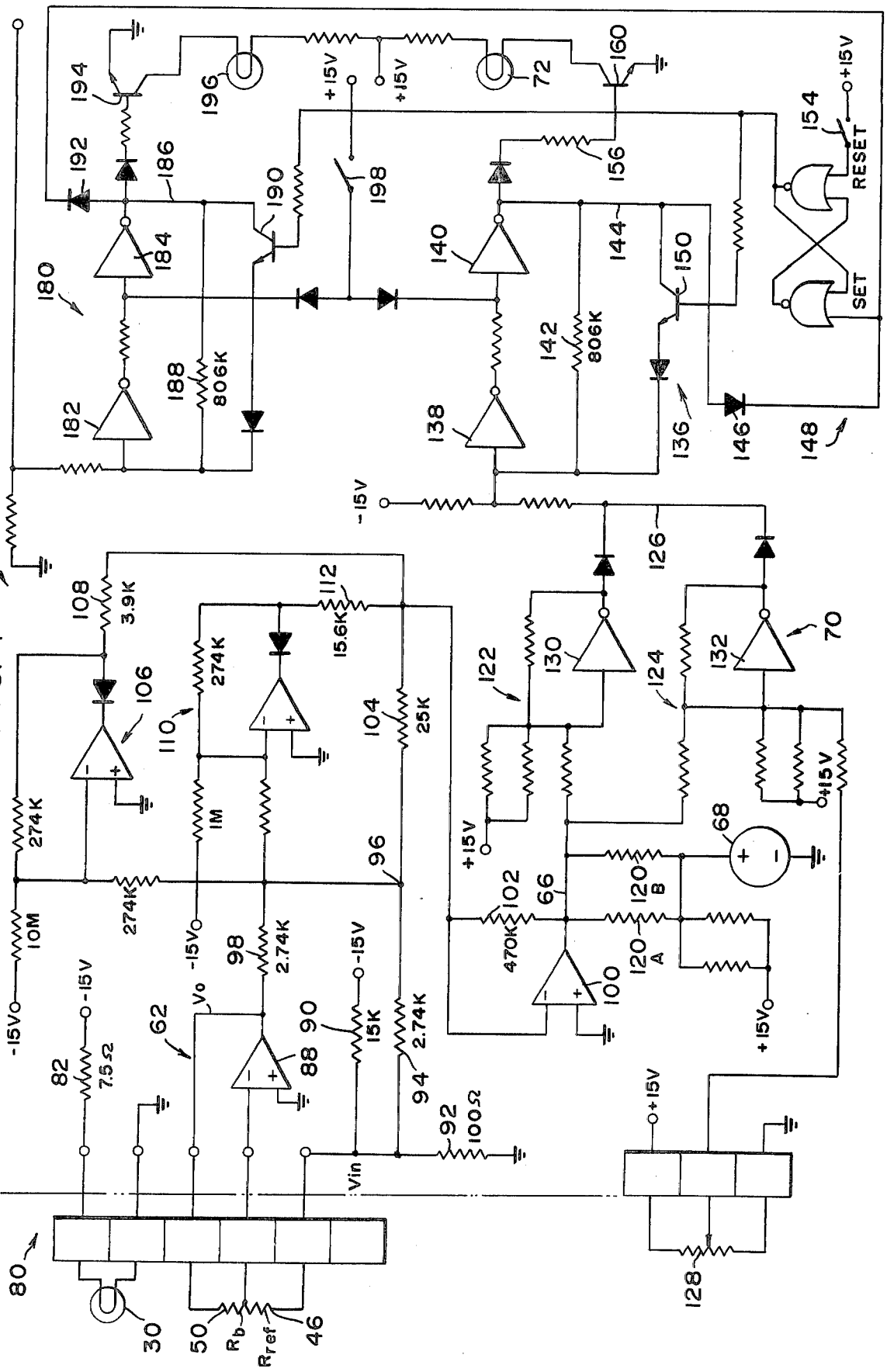
FIG. 4 is a schematic diagram of circuits employed in the arrangement of FIG. 1.

As shown in FIG. 4, the detection circuitry 80 for the blood leak detection system 10 includes the ratio detector 62, linearizer 64, meter 68, failure limit detector 70, and lamp indicator 72. The illumination source lamp 30 is coupled through a 7.5 ohm resistor 82 to −15 volts.

The ratio detector 62 includes an operational amplifier 88 having a negative input coupled through the resistance of the reference photo cell 46 and then through a three-way parallel combination of a 15K resistor 90 to −15 volts, a 100 ohm resistor 92 to ground and a 2.74K resistor 94 to an output 96 of the ratio detector circuit 62. The resistors 90 and 92 operate through voltage divider action to drive resistance $R_{ref}$ with a small negative voltage, $V_I$, equal to approximately −0.1 volt. The output of amplifier 88 is coupled through a 2.74K resistor 98 to the output 96 of ratio detector circuit 62. The positive input to amplifier 88 is coupled to ground. This creates a virtual ground at the negative input. Resistances $R_b$ and $R_{ref}$ are normally on the order of 10K during blood leak detector operation. Resistance $R_b$ is coupled as a feedback resistance between the output of amplifier 88 and the negative input so that the output of amplifier 88, is $V_0 = R_b/R_{ref} \times V_I$. Under normal conditions, $R_b = R_{ref}$ so that $V_0 = -V_I$ and the voltage divider action of equal resistances 94 and 98 maintain the ratio detector output 96 at approximately ground potential. In the event that blood enters the blood leak detector 60, the resulting decrease in incident light upon photocell 50 causes resistance $R_b$ to be substantially increased with a corresponding increase in the output 96 of ratio detector 62.

The output 96 of ratio detector 62 is coupled through a linearizing circuit 64 which includes a summing junction coupled to the negative input of an operational amplifier 100. The output of amplifier 100 is the system output signal 66 which is fed back through a 470K resistor 102 to the negative input of amplifier 100. The positive input of amplifier 100 is coupled to ground.

As one summing input, the voltage at the output 96 of ratio detector 62 is coupled through a 25K resistor 104 to the negative input of amplifier 100. Output signal 96 is also coupled through a unity gain threshold amplifier circuit 106. Threshold amplifier circuit 106 provides a negative output voltage equal to the extent that signal 96 exceeds approximately 0.41 volts. This negative output voltage is coupled through a 3.9K resistor 108 to the negative input of amplifier 100 and substracts from the signal coupled through resistor 104. Similarly, a second unity gain threshold circuit 110 is coupled to provide a negative output voltage equal to the difference between the voltage of output signal 96 and approximately 4.1 volts. This negative output voltage of threshold amplifier 110 is coupled through a 15.6K resistor 112 to the input of amplifier 100 to further subtract from the ratio detector output signal 96 which is coupled through resistor 104. The unity gain threshold amplifier circuits 106 and 110 of linearizer circuit 64 compensate for the increase in resistance $R_b$ which tends to be greater than linear as the incident light on photocell 50 decreases. The output signal 66 from amplifier 100 is coupled through and approximately 5K resistance 120A, 120B to a meter 68 which may be a milliameter having a scale calibrated in appropriate units such as milligram percent. Meter 68 provides a linear indication of blood leakage.

The output 66 is also coupled to a pair of threshold detectors 122, 124. Threshold detector 122 causes generation of an alarm signal at an output 126 when signal 66 exceeds a fixed, factory selected threshold. The output of threshold circuit 124 is ORed with the output of circuit 122 to generate alarm signal 126 whenever the magnitude of signal 66 exceeds an operator determined threshold which is selected by potentiometer 128. This double detector alarm circuit arrangement permits the threshold detection level to be operator selected by threshold detector 124 while eliminating the dangerous possibility that the alarm circuit might be unwittingly disabled by the accidental setting of the threshold at too high a magnitude. The threshold detectors 122 and 124 thus provide both adjustable and absolute maximum threshold sensing levels. Threshold circuits 122 and 124 are implemented with inverters 130, 132 which may be implemented as suitable logic elements such as C-mos inverters which are compatible with the +15 volt source used to energize the operational amplifiers in the circuit 80.

Normally the output 66 of amplifier 100 is at an approximately zero potential. However, in the event that blood enters the chamber 16, signal 96 becomes positive and signal 66 becomes negative. If signal 66 become sufficiently negative one of the inverters 130, 132 becomes activated and its normally low output switches to a high voltage to drive alarm signal 126 high. The output alarm signal 126 is coupled to drive a latching circuit 136. When signal 126 goes high the input to an inverter 138 goes high to drive the output low and in turn drive the input to an inverter 140 low. A 806K positive feedback resistor 142 is coupled between the output of inverter 140 and the input of inverter 138 to provide hysteresis and help hold the alarm indication in latched condition to provide stability. An alarm output signal 144 at the output of inverter 140 is coupled through a diode 146 to drive a set input of a latch circuit 148. When latch circuit 148 becomes set, it drives the base of a transistor 150 having the collector and emitter thereof coupled between output 144 and the input to inverter 138 to latch thealarm condition until the latch 148 is reset by manual activation of a switch 154. The latched alarm output signal 144 is also coupled through a resistance 156 to drive the base of a transistor 160 which operates as a lamp driver switch for alarm indicator lamp 72. A second alarm latching circuit 180 is responsive to a bubble trap signal indicating that the bubble trap is not working properly to cause the normally low input to an inverter 182 to go high, to drive the input of an inverter 184 coupled thereto low and drive the bubble latch circuit output 186 at the output of inverter 184 high. A 806K positive feedback resistor 188 is coupled between output 186 and the input to inverter 182 and a transistor 190 having its base input coupled to the output of latch 148 also has its collector coupled to output 186 and its emitter coupled to the input to inverter 182. The output 186 of bubble trap latch circuit 180 is coupled through a diode OR gate 192 to the set input of latch 148. Thus, once a positive output signal is generated at output 186, the latch 148 is set to turn on transistor 190 and maintain the alarm signal in a latched condition until latch 148 is reset by activation of switch 154. The output 186 is also coupled to the base of a lamp driver transistor 194 which causes illumination of a bubble trap alarm indicator 196 whenever the output signal 186 goes high.

A rinse switch 198 selectively couples a 15 volt source to the inputs of inverters 140 and 184 to artificially hold the inputs high and thus the outputs low to prevent an alarm indication signal during maintenance operation such as rinsing when it is desired to maintain the system in a normal operating mode even though an alarm condition may be detected.

While there has been shown and described above a particular arrangement of a blood leak detector system in accordance with the invention for the purpose of enabling a person of ordinary skill in the art to make and use the invention, it will be appreciated that the invention is not limited thereto. Accordingly, any modifications, variations, or equivalent arrangements within the scope of the attached claims should be considered to be within the scope of the invention.

That which is claimed is:

1. A system for detecting the presence of hemoglobin in a solution comprising:

a radiant energy transmissivity cell including a sample chamber extending along an inclined optical axis between an upper end and an opposite lower end, the sample chamber having a fluid inlet at one end of the chamber for receiving a continuous flow of said solution, a fluid outlet at an end opposite said one end for continuously expelling said solution and a gas outlet positioned at an uppermost portion of the chamber at the upper end to continuously expel gas that accumulates at the gas outlet;

first and second light transmissive windows positioned at opposite ends of the sample chamber;

a light source positioned proximate an end of the sample chamber to emit radiant energy along the optical axis through the first and second windows and through the sample chamber;

first and second radiant energy detectors each positioned proximate an end of the sample chamber opposite the light source to receive radiant energy emitted by the light source after the energy has passed through the first and second windows and the sample chamber, and to generate an indication of the radiant energy incident thereon;

a bandpass optical filter disposed along a light path between a window at an end of the sample chamber proximate the first and second detectors and one of the detectors, the filter having a pass band centered at a wavelength at which hemoglobin constituents of blood are highly light absorbent; and ratio detecting means responsive to the first and second radiant energy detectors for indicating the ratio of the indications of said detectors.

2. The invention as set forth in claim 1 above, wherein said light source provides a light spectrum encompassing the range of 4200 A to 4500 A, and wherein said bandpass filter means transmits a substantially narrower bandwidth at approximately 4200 A.

3. The invention as set forth in claim 2 above, wherein said light source provides substantial light energy at the 5000 A region.

4. The invention as set forth in claim 3 above, wherein said bandpass filter means and a first detector are disposed along the optical axis, and wherein the second detector is disposed at an angle to the optical axis, and wherein the transmissivity cell further includes a diffuse light transmitting element transverse to the optical axis and between said light source and said first and second detector means.

5. The invention as set forth in claim 4 above, wherein said transmissivity cell includes a sample chamber defining housing having inlet and outlet portions at lower and upper ends respectively.

6. The invention as set forth in claim 1 above, wherein said first and second radiant energy detectors comprise photoresistive elements, and wherein said ratio detecting means comprises an operational amplifier including said photosensitive elements in different feedback and input circuits respectively with the ratio of the resistances of said photosensitive elements being indicated by a voltage at an output of said operational amplifier.

7. A system for detecting the presence of hemoglobin in a solution comprising:

a sample cell defining a cylindrical sample chamber which extends along a central optical axis that is inclined with respect to the horizontal between opposite upper and lower ends, the sample chamber having a fluid inlet disposed at one end for continuously receiving solution, a fluid outlet disposed at an end opposite the one end for continuously discharging solution, and a gas outlet disposed at an uppermost portion of the upper end of the chamber to discharge gases collecting thereat, the sample cell providing a single light transmissive path along the optical axis through the sample cell and fluid therein;

a single radiant energy source coupled to continuously emit broadband radiant energy along the single light path through the sample cell and fluid therein;

a first radiant energy detector positioned along the optical axis to receive radiant energy from the energy source after the radiant energy passes through the sample chamber and a fluid therein;

a second radiant energy detector positioned in spaced apart relationship to the optical axis, the second radiant energy detector being optically coupled to a point along the optical axis between the sample cell and the first radiant energy detector by a relatively long, small cross-sectional filter free light path;

an optical filter disposed along the light path between said point along the optical axis and the first radiant energy detector to pass only a narrow band of radiant energy to the first radiant energy detector which is readily absorbed by hemoglobin in a fluid within the sample cell; and a ratio circuit coupled to the first and second radiant energy detectors to provide an output that is indicative of a ratio of radiant energy that is incident upon the first and second radiant energy detectors.

8. The invention as set forth in claim 7 above, wherein said first and second radiant energy detectors comprise first and second photosensitive resistive elements respectively, and wherein said ratio circuit comprises an operational amplifier having the second resistive element connected to an inverting input and the first resistive element connected between an output and said inverting input.

9. The invention as set forth in claim 7 above, further comprising an operational amplifier, wherein the first radiant energy detector is a photosensitive resistive means, wherein the first photosensitive resistive means is responsive to a relatively narrow band signal, and is coupled in a negative feedback circuit of said operational amplifier, and wherein said second detector means is responsive to a relatively broad wavelength band and is coupled in the input circuit of said operational amplifier, such that said operational amplifier provides the ratio of said narrow wavelength band signal to said broad wavelength band signal.

10. The invention as set forth in claim 9 above, including linearizer circuit means coupled to the output of said operational amplifier, said linearizer circuit means including summing circuit means and at least one operational amplifier means coupled to provide a subtractive signal to said summing circuit means for output signals from said operational amplifier in excess of a selected level.

11. The invention as set forth in claim 10 above, including means responsive to said linearizer circuit means for providing a responsive output voltage, and further including means responsive to the output voltage for indicating the presence of output voltages in excess of a selectable threshold, and alarm circuit means responsive to indications in excess of a selective threshold for providing a steady state indication of the occurrence of an alarm condition.

12. The system according to claim 7 above, further comprising an alarm circuit coupled to compare the output to a selected threshold and provide an alarm indication when the output exceeds the selected threshold, said alarm circuit including a memory circuit responsive to an alarm indication for causing the alarm circuit to continue an alarm indication once started until the memory circuit is selectively reset.

13. The system according to claim 7 above, wherein the first and second radiant energy detectors are first and second photocells respectively, each having a resistance which decreases with the intensity of radiant energy incident thereon, the first photocell having incident thereon only light passing through the sample cell at a narrow band of frequencies with a wavelength of approximately 4200 A, the second photocell having incident thereon light passing through the sample cell with a band of frequencies which includes frequencies having wavelengths within the range of 4700 A to 5000 A.

14. A system for detecting the leakage of blood into a solution comprising:
 an elongated chamber having an upper surface inclined with respect to a horizontal plane and extending between upper and lower light transmissive ends, the chamber including a solution inlet proximate the lower end, a solution outlet proximate the upper end and a bubble outlet proximate the upper end and the upper surface;
 a light source disposed to shine light upon one end of the chamber and through the chamber to an opposite end;
 a first photosensor disposed to detect the incidence thereon of light which passes through the chamber from the light source at only frequencies that are readily absorbed by blood within a solution passing between the solution inlet and outlet of the chamber;
 a second photosensor disposed to detect the incidence thereon of light which passes through the chamber from the light source at frequencies that are not readily absorbed by blood within a solution passing between the solution inlet and outlet of the chamber; and
 a circuit coupled to detect and indicate relative changes in the intensity of sensed light incident upon the first and second photosensors.

15. The system according to claim 14 above, wherein the circuit includes a light failure circuit coupled to detect the failure of normal light intensities to pass through the chamber to the first and second photosensors.

16. The system according to claim 14 above, wherein the circuit includes a latching circuit causing an indication of a relative change in the intensity of sensed light to be continued, once started, until selectively discontinued without regard to the relative change in the sensed light.

17. The system according to claim 14 above, wherein the circuit indicates a relative change in the intensity of sensed light when the ratio of intensity of light sensed by the first photosensor relative to the intensity of light sensed by the second photosensor exceeds a selected threshold.

* * * * *